United States Patent [19]

Conero

[11] Patent Number: 5,106,375
[45] Date of Patent: Apr. 21, 1992

[54] DYNAMIC LEAD SCREW ENGAGEMENT AND INDICATOR

[75] Inventor: Ronald S. Conero, San Diego, Calif.

[73] Assignee: IVAC Corporation, San Diego, Calif.

[21] Appl. No.: 704,337

[22] Filed: May 23, 1991

[51] Int. Cl.$^5$ .............................................. A61M 5/20
[52] U.S. Cl. .............................. 604/155; 128/DIG. 1; 604/67
[58] Field of Search ................................. 604/67, 155; 128/DIG. 1, DIG. 12

[56] References Cited

U.S. PATENT DOCUMENTS

| | | |
|---|---|---|
| 3,235,220 | 2/1966 | Rantsch et al. . |
| 3,701,345 | 10/1972 | Heilman ................................. 604/155 |
| 3,720,211 | 3/1973 | Kyrias ................................... 604/155 |
| 3,757,591 | 9/1973 | Taylor . |
| 3,842,690 | 10/1974 | Gulick . |
| 3,858,581 | 1/1975 | Kamen . |
| 3,886,938 | 6/1975 | Szabo et al. . |
| 4,023,431 | 5/1977 | Pavlas . |
| 4,125,049 | 11/1978 | Price, Jr. . |
| 4,191,187 | 3/1980 | Wright . |
| 4,424,720 | 1/1984 | Bucchianeri . |
| 4,435,173 | 3/1984 | Siposs et al. . |
| 4,465,474 | 8/1984 | Mardorf . |
| 4,544,369 | 10/1985 | Skakoon et al. . |
| 4,560,979 | 12/1985 | Rosskopf . |
| 4,662,872 | 5/1987 | Came ............................ 128/DIG. 1 |
| 4,685,903 | 8/1987 | Cable et al. . |
| 4,731,058 | 3/1988 | Doan ....................................... 604/155 |
| 4,767,406 | 8/1988 | Wadham et al. ......................... 604/155 |
| 4,804,368 | 2/1989 | Skakoon et al. ......................... 604/155 |
| 4,883,101 | 11/1989 | Strong ..................................... 604/155 |
| 4,908,017 | 3/1990 | Howson et al. . |
| 4,919,650 | 4/1990 | Feingold et al. . |
| 4,931,041 | 6/1990 | Faeser ..................................... 604/155 |
| 4,952,205 | 8/1990 | Mauerer et al. . |
| 4,959,056 | 9/1990 | Dombrowski et al. . |
| 4,988,337 | 1/1991 | Ito . |
| 5,006,112 | 4/1991 | Metzner . |
| 5,034,004 | 7/1991 | Crankshaw ............................ 604/67 |

FOREIGN PATENT DOCUMENTS

| | | |
|---|---|---|
| 0354852 | 2/1990 | European Pat. Off. . |
| 3314664C2 | 2/1985 | Fed. Rep. of Germany . |
| WO90/10468 | 9/1990 | PCT Int'l Appl. . |
| 1475673A1 | 4/1989 | U.S.S.R. . |

*Primary Examiner*—Paul J. Hirsch
*Attorney, Agent, or Firm*—Fulwider, Patton, Lee & Utecht

[57] ABSTRACT

Automatic engagement of a lead screw with a lead screw drive mechanism. A plunger driver used to move the plunger of a syringe is connected to the screw drive mechanism. A first detector provides a plunger signal indicating the presence of a syringe plunger in the plunger driver and a second detector provides a thread engagement signal indicating engagement or disengagement of the lead screw drive mechanism with the lead screw. The thread engagement detector monitors movement of a rigid linkage at the screw drive mechanism which has a nonlinear characteristic curve. In the case where the plunger signal indicates the presence of a plunger and the thread engagement signal indicates engagement of the drive mechanism with the lead screw, the lead screw is rotated in a forward direction to remove the thread clearance. In the case where the thread engagement signal indicates disengagement of the drive mechanism with the lead screw, the processor rotates the lead screw first in a reverse direction and then in a forward direction to cause engagement of the threads.

19 Claims, 6 Drawing Sheets

DYNAMIC LEAD SCREW ENGAGEMENT AND INDICATOR

BACKGROUND

The invention is related generally to screw drive mechanisms, and more particularly, to a lead screw engagement system.

The infusion of fluids such as parenteral fluids into the human body is accomplished in many cases by means of a syringe pump having a lead screw on which a screw drive mechanism is mounted. Rotation of the lead screw is translated into linear motion by the screw drive mechanism and is transmitted to the syringe plunger by a plunger driver. The plunger driver is typically rigidly connected to the screw drive mechanism. A split nut or half nut is used as part of the screw drive mechanism in some pumps for easy and rapid repositioning of the screw drive mechanism and plunger driver on the lead screw to engage a new syringe plunger. An activating lever or other mechanical interface may be provided at the plunger driver to separate the split nut from the lead screw threads and to disengage the plunger driver from the present syringe plunger. The plunger driver is retracted and the syringe replaced. The operator uses the activating lever or other mechanical interface to disengage the split nut from the lead screw, moves the plunger driver and split nut along the lead screw to the appropriate position and inserts the new syringe plunger. The operator then releases the activating lever to clamp the plunger driver onto the new plunger and to engage the lead screw threads with the split nut. Unfortunately, re-engagement with the lead screw threads does not always occur at this time due to the shape of the thread profile.

Figure 1:
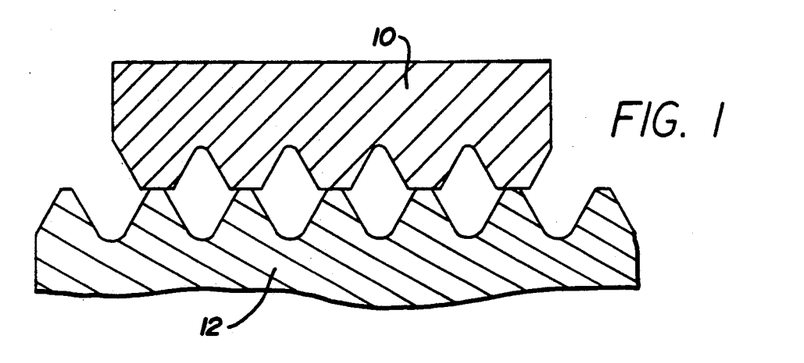
FIG. 1 presents a cross-sectional view of the crests of the threads of the split nut resting on the crests of the threads of the lead screw.

As shown in FIG. 1, in some cases the crests of the threads 10 of the split nut align with and contact the crests of the threads 12 of the lead screw rather than the threads engaging each other. Because these threads may be relatively flat at their crests, they do not engage each other until the lead screw has turned a sufficient amount and the bias device of the screw drive mechanism has forced the threads of the split nut to drop into or engage the lead screw threads. Under low infusion rates, such sufficient lead screw rotation may take a substantial amount of time, this time then being a period during which the patient does not receive the infusion fluid.

Figure 2:
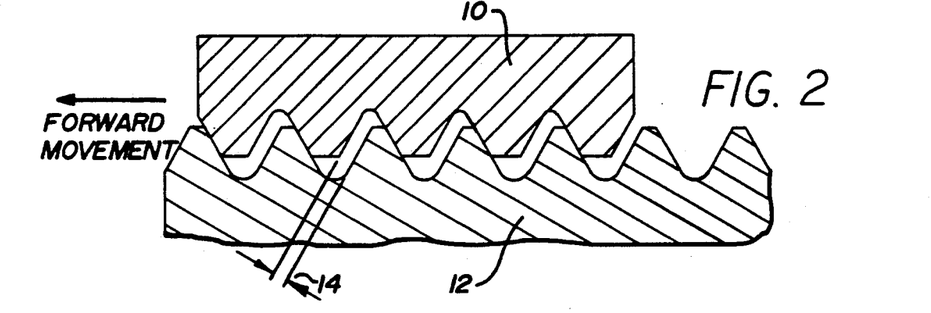
FIG. 2 presents a cross-sectional view of the non-driving surfaces of the split nut threads engaging the non-driving surfaces of the lead screw threads and shows thread clearance.

In another case as presented in FIG. 2, the non-driving surfaces of the threads 10 of the split nut may contact the non-driving surfaces of the threads 12 of the lead screw when the activating lever is released. The arrow indicates the direction of forward movement of the split nut and plunger driver. Due to the thread clearance 14 between the two sets of threads, some amount of time may pass before the driving surfaces of the lead screw threads 12 contact the driving surfaces of the split nut threads 10 and actually begin to move the split nut and plunger driver. This also would be a time period during which the patient receives no infusion fluids.

Figure 3:
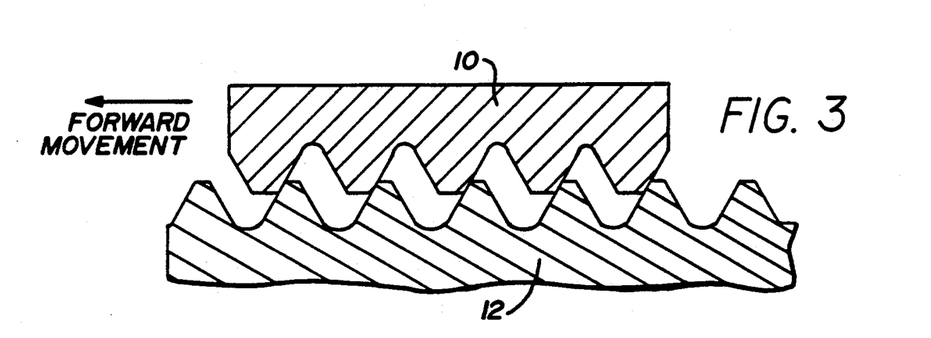
FIG. 3 presents a cross-sectional view of a partial engagement of the split nut threads with the lead screw threads.

In yet another case as presented in FIG. 3, the threads 10 of the split nut may have only partially engaged the threads 12 of the lead screw. If this should happen on the driving surfaces of the threads of the lead screw as shown, the threads 10 of the split-nut may not drop into the threads 12 of the lead screw because of the large amount of back pressure provided by the full syringe and because of the force vector developed by the lead screw threads which tends to force the split nut threads 10 up and out of the lead screw threads 12. If the biasing force on the split nut is not strong enough to overcome all of these factors, the split nut threads 10 may be forced out of contact with the driving surfaces of the threads 12 of the lead screw and into the position shown in FIG. 1. This case would likewise result in a time period during which the patient would not receive the infusion fluid and this time period may exceed that associated with FIG. 1.

In certain prior systems having a detector to indicate thread engagement between the lead screw and the screw drive mechanism, the case shown in FIG. 3 may be indicated as thread engagement. In many of these prior systems, the detector monitors the position of the lever used by the operator at the plunger driver rather than the engagement mechanism at the lead screw itself. And in some cases, these levers are coupled to the split nut through a spring rather than through a rigid mechanical connection. Where the lever is in the correct position for engagement of the screw drive mechanism with the lead screw but the spring coupling has not transmitted the lever force to the split nut, an inaccruate indication of screw engagement may be given with a resulting time period during which the patient receives no infusion fluid.

Hence, those skilled in the art have recognized a need for an lead screw engagement system in which the screw drive mechanism and lead screw are made to engage as soon as possible so that no delay in fluid infusion occurs. Further, a need for a more accurate and reliable indicator of engagement has been recognized. The invention fulfills these needs.

SUMMARY OF THE INVENTION

The present invention provides for the automatic engagement of a lead screw drive mechanism with a lead screw. Associated with the screw drive mechanism is a plunger driver used to move the plunger of an inserted syringe. The screw drive mechanism includes an engagement mechanism which causes the threads of the screw drive mechanism to selectively engage and disengage the threads of the lead screw. An engagement detector is used to determine the position of the engagement mechanism and provdies a signal representative of its position as regards engagement of the threads. A second detector provides a plunger signal indicating the presence of a syringe plunger in the plunger driver. A processor receives the plunger signal and the thread engagement signal and provides a signal to the motor controller to cause the motor to rotate the lead screw in response thereto.

In the case where the plunger singal indicates the presence of a plunger and the thread engagement signal indicates engagement of the drive mechanism with the lead screw, the processor causes the motor to rotate the screw in a forward direction by a first predetermined amount to remove the thread clearance.

In the case where the plunger signal indicates the presence of a plunger and the thread engagement signal indicates disengagement of the drive mechanism with the lead screw, the processor causes the motor to rotate first in a reverse direction for a second predetermined amount and then in a forward direction for a third predetermined amount to cause engagement of the threads. In the event that the thread engagement signal indicates engagement of the threads during the reverse rotation phase of the screw, the processor will then continue reverse rotation for an additional predetermined distance to fully seat the threads. For this condition, the threads are already on the driving surfaces and the thread clearance has been removed. In the event that the thread engagement signal indicates engagement during the forward screw rotation phase, the processor will continue forward rotation for an additional predetermined distance to fully seat the threads and remove thread clearance. The processor will then await further pump operation instructions.

The cycle of reverse and then forward rotation of the lead screw is limited in the distance of travel along the lead screw. The cycle of reverse/forward screw rotation may be repeated a limited number of times to attempt to attain screw engagement. Failure to attain engagement within the limit results in an unengaged system.

The engagement detector is mounted to detect the position of the engagement mechanism which is rigidly connected to the threads of the screw drive mechanism. The detector is thus connected to the acutal mechanical connection to the threads and is therefore more reliable and more accurate in determining actual engagement. Furthermore, the trip point of the detector is selected to be at a point which is less than fifty percent of the root thread depth thereby assuring that a "threads engaged" signal indicates that the threads are engaged sufficiently to cause a movement of the plunger driver.

Other aspects and advantages of the invention will become apparent from the following detailed description and the accompanying drawings, illustrating by way of example the features of the invention.

DETAILED DESCRIPTION OF THE PREFERRED EMBODIMENTS

Figure 4:
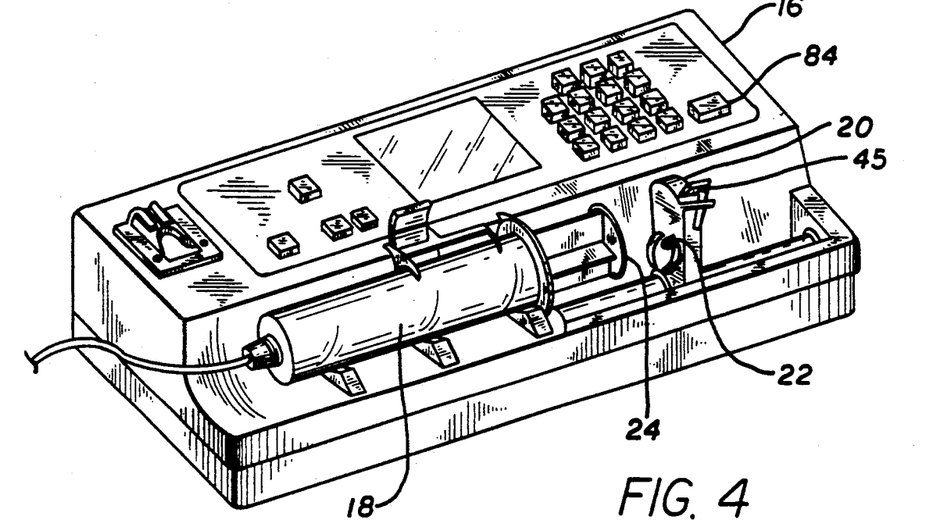
FIG. 4 is a perspective view of a syringe pump showing a syringe installed and a plunger driver with a plunger detector not coupled to the syringe plunger.

Referring now to the drawings with more particularity wherein like reference numerals designate like or corresponding elements among the several views, there is shown in FIG. 4 a syringe pump 16 having a syringe 18 partially installed and a plunger driver 20. The plunger driver 20 includes a plunger detector button 22 which is used to detect the presence of a syringe plunger 24 engaged with the plunger driver 20. In FIG. 4, the syringe plunger 24 is not engaged with the plunger driver so that the detector button 22 may be seen.

Figure 5:
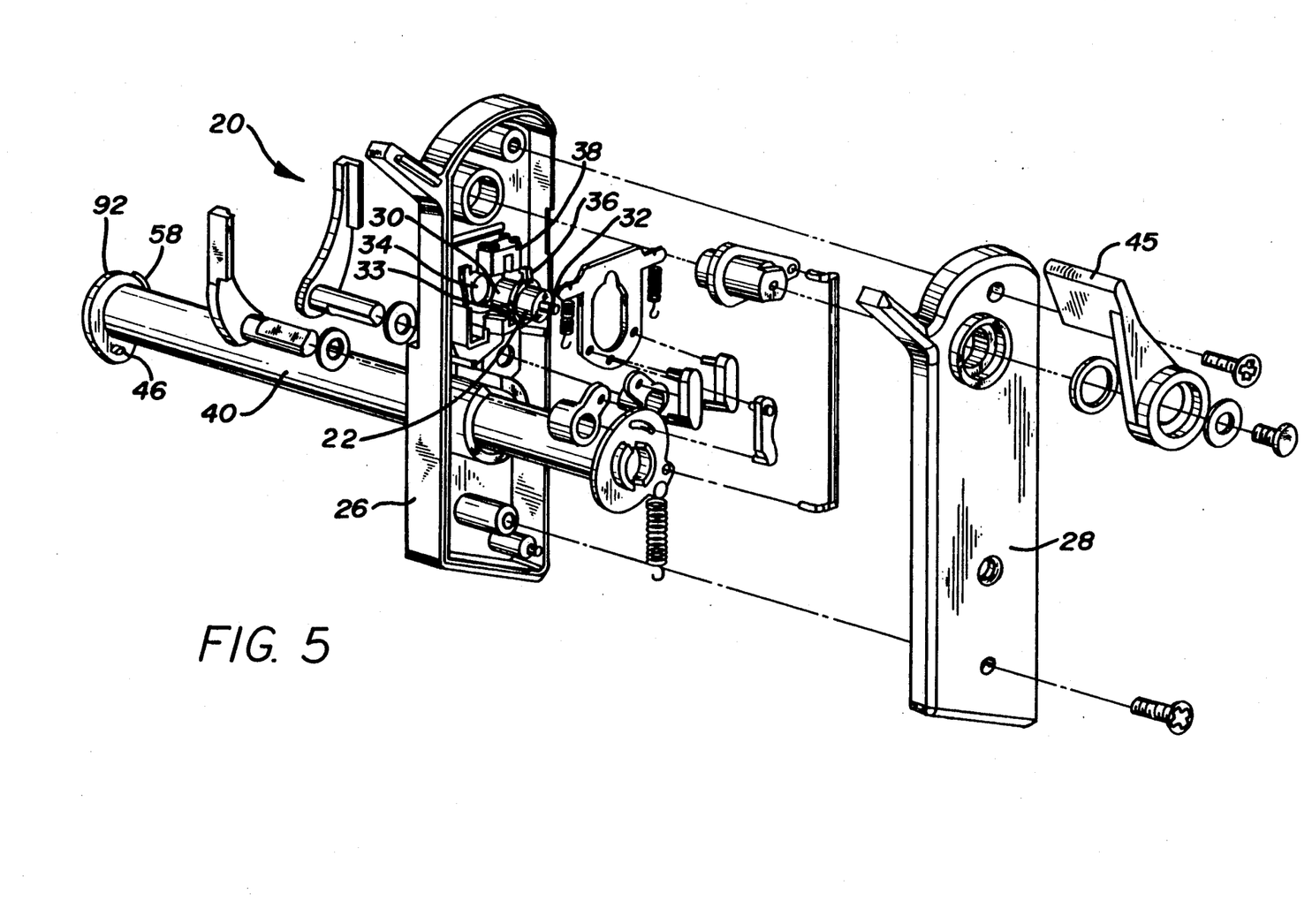
FIG. 5 is an exploded view of the plunger driver showing the plunger detector of FIG. 4.

Referring now to FIG. 5, an exploded view of a plunger driver is shown. The front housing 26 has been separated from the rear housing 28 to view the plunger detector in more detail. In this figure, the detector button 22 has been withdrawn from its normal position in the front housing 26. The button 22 has a beveled front surface 30 to allow additional flexibility in loading the syringe. The button has a spring 32 to provide a bias of the button outward toward the syringe plunger. In this embodiment, the spring rests against the rear housing 28 to push the button 22 to extend out of the front housing through aperture 34. The button includes an annular stop flange 33 to retain the button in the housing. The button will extend through the apreture 34 formed in the front housing to press against an inserted syringe plunger 24 (FIG. 1).

The button 22 also includes a flag 36 for indicating the button's position and that of the syringe plunger. An optical beam detector 38 is mounted above the button 22 but in line with the flag 36 to determine the position of the flag. In this embodiment, should the button be extended as far forward as possible, the flag 36 will interrupt the beam of the optical beam detector 38 and the detector will provide a signal indicating that no plunger is present. As shown, the plunger driver 20 is connected to a split nut tube 40.

Figure 6:
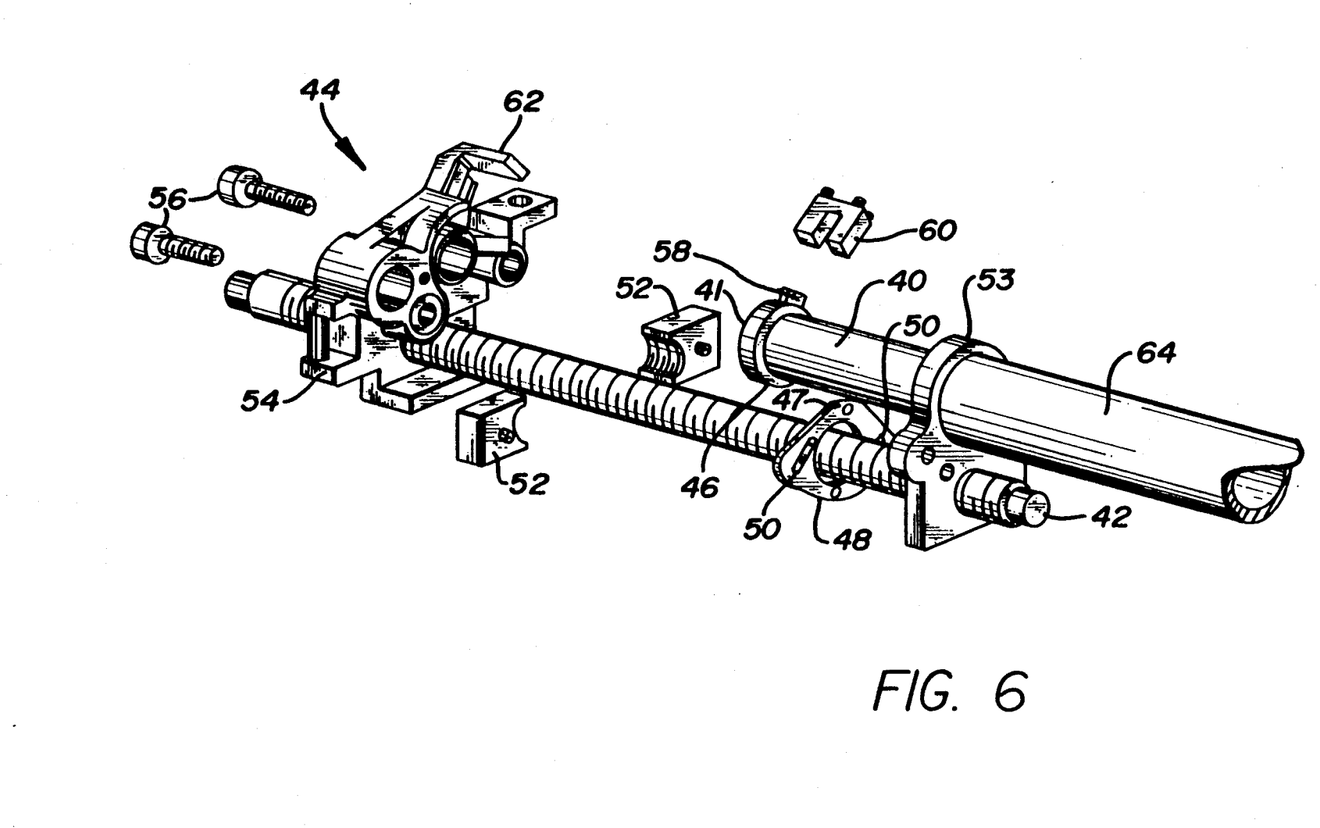
FIG. 6 is an exploded view of a lead screw and screw drive mechanism showing a thread engagement detector in accordance with the principles of the invention.

Referring now to FIG. 6, a lead screw 42 is shown and mounted to that screw is a screw drive mechanism 44. The screw drive mechanism 44 includes the split nut tube 40 having a flange 41 on which is mounted a pin 46 for engaging a cam plate 48. The cam plate 48 includes two slots 50, each for engaging a pin on a respective split nut 52 half. The split nut 52 and cam plate 50 are sandwiched between the support plate 53 and the split nut housing 54 and held in position by screws 56. The split nut tube 40 includes a flag 58 rigidly mounted on the flange 41 and the pin 46 and this flag 58 will rotate with the rotation of the tube 40.

The pin 46 on the flange 41 engages the upper slot 47 in the cam plate 50 and thereby rotates the cam plate, and that cam plate will cause motion of the split nut 52 into and out of engagement with the lead screw 42. This arrangement results in a nonlinear movement of the split nut as will be discussed in more detail following. The position of the flag 58 will be representative of split nut engagement with the lead screw 42. Accordingly, an optical beam detector 60 is mounted on a flange 62 forming part of the split nut housing 54 and detects the position of the flag 58. The optical detector 60 provides a thread engagement signal representative of that detection. In the embodiment of FIG. 6, interruption of the beam by the flag 58 will indicate that the split nut 52 is disengaged from the lead screw 42.

In the embodiment of FIG. 6, the support plate 53 is in threaded engagement with the lead screw 42 and will exhibit linear motion as a response to lead screw rotation. The split nut tube 40 and the drive tube 64 (not shown in FIG. 5) rigidly couple the screw drive mechanism 44 to the plunger driver 20. Thus, the plunger driver 20 will move with the screw drive mechanism 44.

Rotation of the split-nut tube 40 and the resulting movement of the split nut halves results from movement of the lever 45 shown in FIGS. 4 and 5. The lever 45 is coupled to the split nut tube 40 as shown in FIG. 5. Thus the flag 58 and detector 60 are immediately and rigidly coupled to the engagement mechanism which causes the halves of the split nut to move. This results in more accurate and more reliable operation of determining thread engagement.

Figure 7:
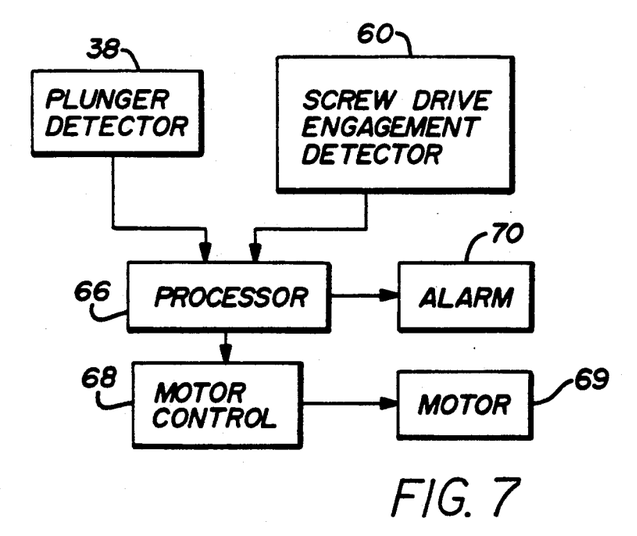
FIG. 7 is a block diagram of a dynamic engagement system in accordance with the principles of the invention.

Referring now to FIG. 7, the detector signals from the plunger detector 38 and from the screw drive engagement detector 60 are coupled to a processor 66. The processor analyzes these signals and based on various factors as discussed below, will provide a signal to the motor control or a flashing indicator 70.

Figure 8:
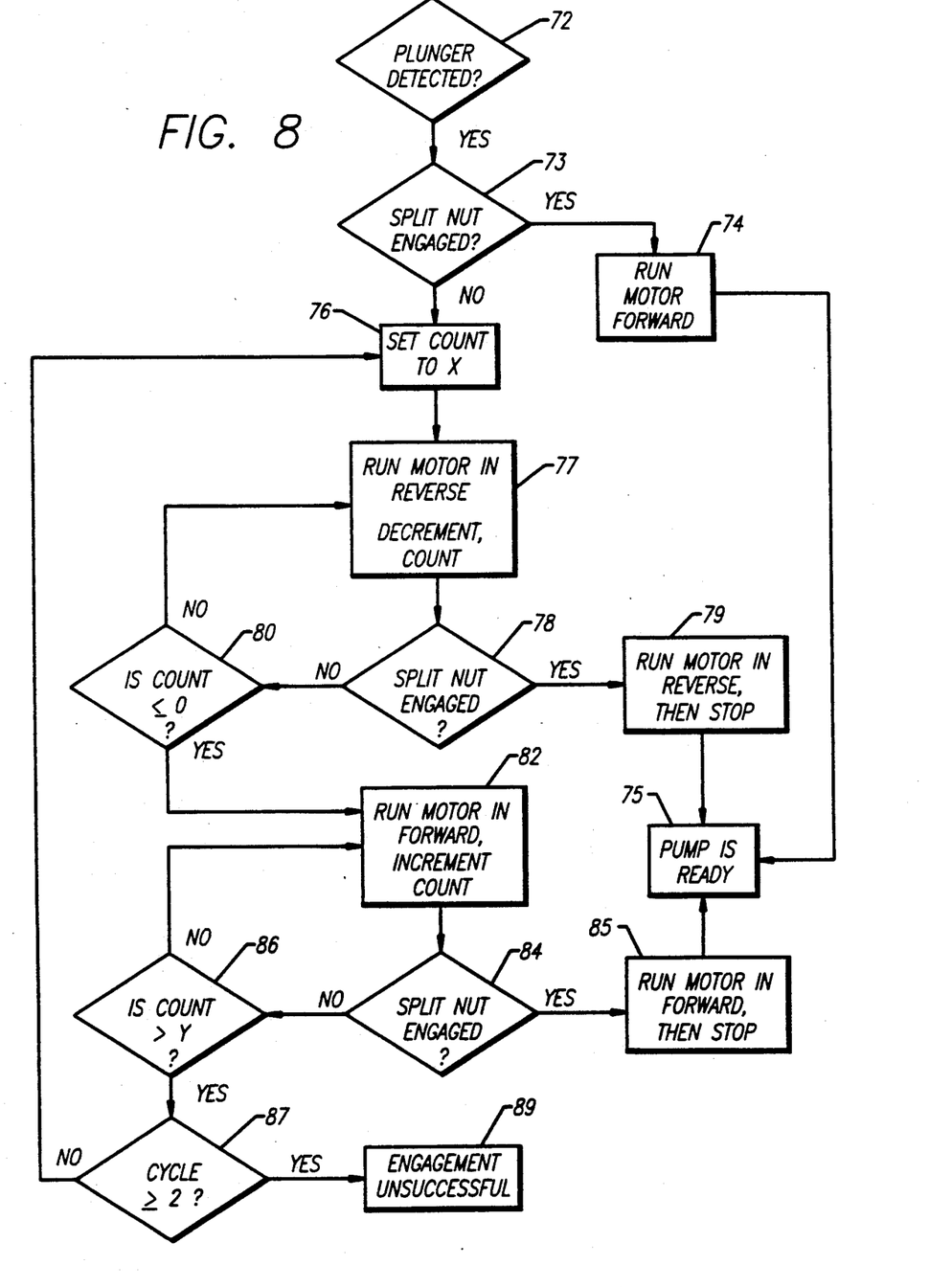
FIG. 8 is a flow chart of a dynamic engagement system in accordance with the principles of the invention.

Referring now to FIG. 8, a flow diagram is presented which illustrates an embodiment. In block 72, the plunger detector signal is analyzed and if the signal indicates that a plunger is present, the engagement detector 60 signal is analyzed 73 to determine if the threads are engaged. If the threads are engaged, the processor 66 causes forward rotation 74 of the motor 69 to remove any thread clearance which may exist between the threads as shown in FIG. 2. In one case where the pitch of the threads was 0.050 inches (1.27 mm), the motor would turn the lead screw by an amount equal to 0.00064 in. (0.0162 mm) of travel along the lead screw which is the distance between the slope of the threads. This would then remove all thread clearance and the driving surfaces of the lead screw threads would be in contact with the driving surfaces of the split nut threads. When the pump is thereafter energized to begin infusion, fluid will immediately flow. The pump is then ready for infusion 75.

If at block 73, the thread engagement detector 60 indicates that the threads are not engaged, the processor 66 would then set 76 a count equal to "X" which may be a count of flags coupled to motor rotation or drive gear rotation or some other measure of distance along the lead screw, and then cause the motor to run in reverse while decrementing the count 77. The screw drive engagement detector 60 signal is analyzed 78 to determine if the threads are engaged, and if they are, the motor is run in reverse 79 for some further time to fully seat the threads. The motor need not be run forward at this time because the driving surfaces of the threads of the lead screw will be against the driving surfaces of the split nut. The pump is now ready 75.

In the event that the threads are not engaged 78, the count is analyzed 80 and if not less than or equal to zero, reverse running of the motor is continued 77 until the count does equal or is less than zero or the threads become engaged. If they still do not engage, the motor is run in forward and the count incremented 82. The engagement detector 60 signal is analyzed 84 to determine if the threads are engaged, and if they are, the motor is run in forward 85 by an amount of twice the thread clearance plus a tolerance amount, which in one embodiment was 0.003 inches (0.076 mm). The pump is then ready 75.

In the event that the threads are not engaged at this time, the count is analyzed 86 and if less than "Y", forward running of the motor is continued 82 until the count does exceed Y or the threads become engaged. If they still do not engage, the number of cycles of reverse/forward running is analyzed 87 and if equal to or greater than two, the thread engagement is considered unsuccessful 89 and a flashing indicator 90 (FIG. 4) continues to be energized. If the cycle count is under two, it is repeated.

In the above mentioned embodiment, the counts "X" and "Y" are set to result in travel along the lead screw of approximately 0.025 in. (0.635 mm). In this embodiment, these distances correspond to the distance of the length of the crest of one lead screw thread plus the distance of the crest of one split nut thread plus a tolerance amount.

In one embodiment, as described by FIG. 8, a limit on the number of cycles of forward/reverse rotation is imposed. In this figure, the limit is two cycles. Another limit which may be imposed is a time limit. For example, the processor may limit the forward/reverse cycling to a total of five seconds. Other limits are possible.

Referring again to FIG. 6, the flag 58 is placed on the same flange 41 that houses the pin 46 used to move the cam plate 50 to separate the split nut 52. Thus, a direct, rigid and immediate mechanical connection exists between the detector 60 of thread engagement and the means to cause that engagement. Both are located on the same flange 41. This results in a highly reliable and more accurate system for indicating thread engagement as opposed to prior systems which monitor the movement of the lever as discussed above.

Figure 9:
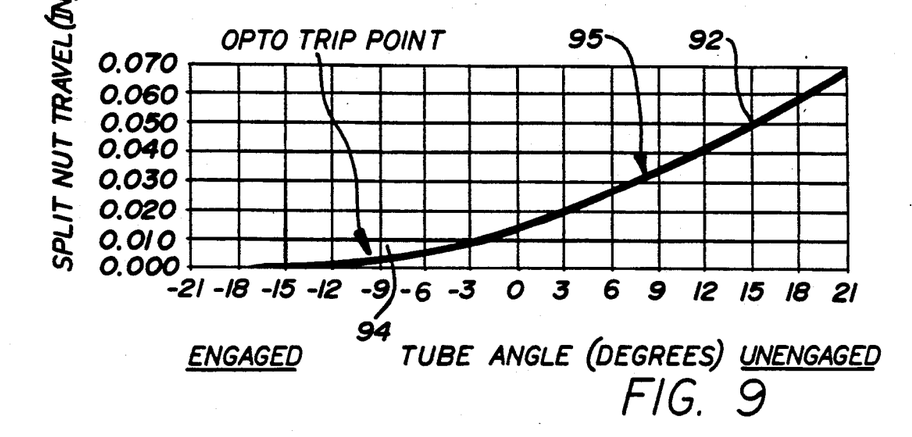
FIG. 9 is a chart of split-nut travel versus drive tube angle showing the point of engagement and the point of detector trip.

Referring now to FIG. 9, a curve of split nut 52 travel versus split nut tube 40 angle is provided. The root thread depth of the lead screw and the split-nut is approximately 0.032 in. (0.825 mm). The split nut and lead screw should begin engagement at approximately 0.059 in. (1.50 mm) in this embodiment. In FIG. 9, the vertical axis represents distance from the center of the lead screw and the horizontal axis represents the angle of rotation of the split nut tube 40. Because a cam plate 48 is used with the pin 46 as shown, a nonlinear curve results and the trip point 94 of the optical detector 60 can be located on the shallow part of the curve which is much less sensitive to the tolerances of the parts than at the steeper part of the curve. This also allows the trip point 94 to be set at a low depth to more accurately indicate actual thread engagement. In this case, the depth of the trip point 94 is 0.003 inches (0.076 mm) which is less than the root thread depth. In this case the root thread depth 95 is approximately 0.032 inches (0.813 mm). It has been found that setting the trip point no higher than fifty percent of the root thread depth results in greater accuracy. In the case shown in FIG. 9, that point would be at approximately 0.016 in. (0.406 mm).

Figure 10A:
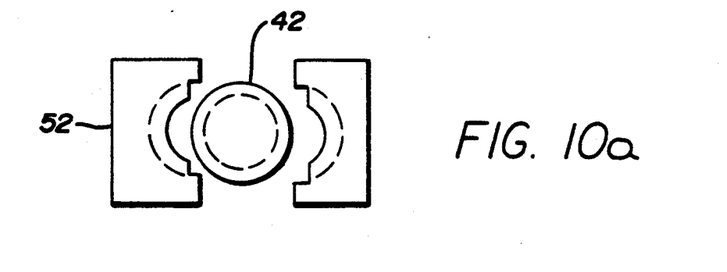
FIGS. 10a and 10b present sequential views of split nut engagement with the lead screw.
Figure 10B:
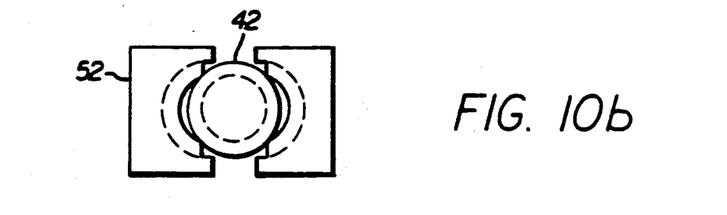

Referring now to FIGS. 10a and 10b, the sequence of a split-nut 52 and lead screw 42 thread engagement can be seen. In FIG. 10a, the split-nut 52 and lead screw 42 are disengaged from each other. The dashed lines indicate root thread depth. In FIG. 10b, some engagement has occurred, but due to the configuration of the split-nut, engagement only at the extremities of the respective halves of the split-nut has occured. This point of engagement is indicated as numeral 92 in FIG. 9. Thus, the main portion of the split-nut threads has not engaged with the lead screw threads. The threads may disengage from each other if a large load is experienced by the plunger driver. Therefore, it is desirable to indicate engagement at a much lower point on the curve shown in FIG. 9. This has been done at point 94 as discussed above.

From the foregoing, it will be appreciated that the engagement system and method in accordance with the principles of the invention provides a positive and rapid way of engaging the lead screw with the screw drive mechanism. The use of a screw drive engagement detector in accordance with the invention results in a more accurate and reliable indication of actual thread engagement.

Although specific embodiments of the invention have been described and illustrated it is clear that the invention is susceptible to numerous modifications and embodiments within the ability of those skilled in the art, and without the exercise of the inventive faculty. Thus, it should be understood that various changes in form, detail and application of the present invention may be made without departing from the spirit and scope of the invention.

We claim:

1. An engagement system for engaging the threads of a lead screw with the threads of a screw drive mechanism, the screw drive mechanism operating to translate the rotational motion of the lead screw into linear motion, the system comprising:
   a motor coupled to the lead screw which selectively rotates the lead screw;
   an engagement mechanism mounted to the screw drive mechanism to selectively move the screw drive mechanism threads into and out of engagement with the threads of the lead screw;
   an engagement detector which senses the position of the engagement mechanism and provides an engagement signal representative of the engagement mechanism being in a position to cause engagement of the threads of the screw drive mechanism with the threads of the lead screw; and
   a processor which receives the engagement signal and controls the motor to cause the lead screw to rotate for a predetermined time period when the engagement signal indicates that the threads are not engaged.

2. The system of claim 1 wherein the processor controls the motor to rotate the screw in a first direction for a first predetermined time period and then in a second direction for a second predetermined time period when the engagement signal indicates that the threads are not engaged.

3. The system of claim 2 wherein the first direction is reverse rotation of the lead screw and the second direction is forward rotation of the lead screw.

4. The system of claim 3 wherein the processor controls the motor to continue rotation in the reverse direction for a selected distance to fully seat the threads when the engagement signal indicates thread engagement during reverse rotation.

5. The system of claim 3 wherein the processor controls the motor to continue rotation in the forward direction for a selected distance to remove any clearance between the driving surfaces of the threads when the engagement signal indicates thread engagement during forward rotation.

6. The system of claim 1 wherein:
   the engagement mechanism has a range of movement between engaged and nonengaged, the range of movement including root thread depth; and
   the engagement detector provides the engagement signal when the engagement mechanism has moved to less than fifty percent of root thread depth remaining.

7. The system of claim 6 wherein the range of movement of the engagement mechanism between engaged and nonengaged is nonlinear.

8. The system of claim 1 further comprising:
   a plunger driver coupled to the screw drive mechanism for engaging the plunger of a syringe;
   a plunger detector which senses the presence of a plunger in the plunger driver and provides a plunger signal representative of the presence of the plunger; and
   the processor controls the motor to rotate only if the plunger signal is present.

9. The system of claim 8 wherein the processor controls the motor to rotate the screw in the reverse direction for a first predetermined time period and then in the forward direction for a second predetermined time period when the engagement signal indicates that the threads are not engaged.

10. The system of claim 9 wherein the processor controls the motor to continue rotation in the reverse direction for a selected distance to fully seat the threads when the engagement signal indicates thread engagement during reverse rotation.

11. The system of claim 9 wherein the processor controls the motor to continue rotation in the forward direction for a selected distance to remove any clearance between the driving surfaces of the threads when the engagement signal indicates thread engagement during forward rotation.

12. An engagement system for engaging the threads of a lead screw with the threads of a screw drive mechanism, the screw drive mechanism operating to translate the rotational motion of the lead screw into linear motion, a plunger driver coupled to the screw drive mechanism to couple the linear motion to the plunger of a syringe, the system comprising:
   a motor coupled to the lead screw which selectively rotates the lead screw;
   an engagement mechanism mounted to the screw drive mechanism to selectively move the screw drive mechanism threads into and out of engagement with the threads of the lead screw;
   an engagement detector which senses the position of the engagement mechanism and provides an engagement signal representative of the engagement mechanism being in a position to cause engagement of the threads of the screw drive mechanism with the threads of the lead screw;
   a plunger detector which senses the presence of a plunger in the plunger driver and provides a plunger signal representative of the presence of the plunger; and
   a processor which receives the plunger signal and the engagement signal and controls the motor to cause the lead screw to rotate for a predetermined time period when the plunger signal is present and when the engagement signal indicates that the threads are not engaged.

13. The system of claim 12 wherein the processor controls the motor to rotate the screw in a first direction for a first predetermined time period and then in a second direction for a second predetermined time period when the engagement signal indicates that the threads are not engaged.

14. The system of claim 13 wherein the first direction is reverse rotation of the lead screw and the second direction is forward rotation of the lead screw.

15. The system of claim 14 wherein the processor controls the motor to continue rotation in the reverse direction for a selected distance to fully seat the threads when the engagement signal indicates thread engagement during reverse rotation.

16. The system of claim 14 wherein the processor controls the motor to continue rotation in the forward direction for a selected distance to remove any clearance between the driving surfaces of the threads when the engagement signal indicates thread engagement during forward rotation.

17. A method for engaging the threads of a screw with the threads of a screw drive mechanism, the screw drive mechanism being of the type which moves along the screw in response to the rotation of the screw, the method comprising the steps of:

mounting an engagement mechanism on the screw drive mechanism to selectively cause engagement of the threads of the screw drive mechanism with the threads of the lead screw;

sensing the position of the engagement mechanism;

providing an engagement signal representative of the position of the engagement mechanism; and selectively rotating the lead screw for a predetermined time period in response to the engagement signal indicating that the engagement mechanism is in a position at which the threads are not engaged.

18. The method of claim 17 further comprising the step of: rotating the screw in a first direction for a first predetermined time period and then rotating the screw in a second direction for a second predetermined time period.

19. The method of claim 18 wherein the first direction is reverse rotation of the lead screw and the second direction is forward rotation of the lead screw.

* * * * *